United States Patent [19]
Poppas et al.

[11] Patent Number: 5,409,481
[45] Date of Patent: * Apr. 25, 1995

[54] LASER TISSUE WELDING CONTROL SYSTEM

[75] Inventors: Dix P. Poppas, New York City, N.Y.; Steven M. Schlossberg, Norfolk, Va.; Theodore J. Choma, Silver Spring, Md.; Scott D. Klioze, Burke, Va.; James H. Boll, San Francisco, Calif.

[73] Assignee: Laserscope, San Jose, Calif.

[*] Notice: The portion of the term of this patent subsequent to Aug. 2, 2011 has been disclaimed.

[21] Appl. No.: 160,247

[22] Filed: Dec. 2, 1993

Related U.S. Application Data

[63] Continuation of Ser. No. 886,779, May 21, 1992, Pat. No. 5,334,191.

[51] Int. Cl.⁶ ............................................. A61N 5/06
[52] U.S. Cl. ........................................ 606/12; 606/8; 606/9; 606/10
[58] Field of Search ............................. 606/8, 10–16, 606/9; 607/89

[56] References Cited

U.S. PATENT DOCUMENTS

| | | |
|---|---|---|
| 4,316,467 | 2/1982 | Muckerheide . |
| 4,672,969 | 6/1987 | Dew . |
| 4,854,320 | 8/1989 | Dew et al. . |
| 4,884,568 | 12/1989 | Hahn . |
| 4,950,268 | 8/1990 | Rink . |
| 4,994,059 | 2/1991 | Kosa et al. . |
| 5,002,051 | 3/1991 | Dew et al. . |
| 5,050,597 | 9/1991 | Daikuzono . |
| 5,057,099 | 10/1991 | Rink .................... 606/12 |
| 5,071,417 | 12/1991 | Sinofsky ................. 606/8 |

FOREIGN PATENT DOCUMENTS

| | | |
|---|---|---|
| 0366856 | 5/1990 | European Pat. Off. . |
| 0423431 | 4/1991 | European Pat. Off. . |
| 2809007 | 9/1979 | Germany . |
| 2829516 | 1/1980 | Germany . |
| 2849543 | 5/1980 | Germany . |
| 3934640 | 10/1989 | Germany . |
| 3934646 | 4/1991 | Germany . |

OTHER PUBLICATIONS

Mordon et al "Development of Controlled . . . ", Medical Instrumentation, Aug., 1987, pp. 222–225.
Mehmet et al, "Tissue Soldering . . . Diode Laser", Journal of Vasc. Surg., vol. 11, No. 5, pp. 718–725, May 1990.
Poppas et al, "Laser Welding in Urethral Surgery: Improved Results with a Protein Solder", The Journal of Urology, Feb. 1988, pp. 415–417.
Ganesan et al, "Urethral Reconstruction Using the Carbon Dioxide Laser: An Experimental Evaluation," The Journal of Urology, Oct. 1989, pp. 1139–1141.
Mordon et al, "Development of Controlled Nd: YAG Laser for Medical Applications", Medical Instrumentation, Aug., 1987, pp. 222–225.
Schlossberg et al, "Tissue Welding with Lasers", Seminars in Urology, Aug. 1991, pp. 206–209.
DaiKuzono et al, "Laserthermia: A New Computer-Controlled Contact Nd: YAG System for Interstitial Local Hyperthermia", Lasers in Surgery and Medicine, 1988, pp. 254–258.
Schlossberg et al, "CO₂ Laser Microsurgery and Welding", Lasers and Urologic Surgery, Joseph A. Smith et al, 1989.

*Primary Examiner*—Stephen C. Pellegrino
*Assistant Examiner*—Michael Peffley
*Attorney, Agent, or Firm*—Killworth, Gottman, Hagan & Schaeff

[57] ABSTRACT

A system for welding tissue by irradiation with laser energy, includes a laser for generating a beam of laser energy and directing the beam toward the tissue so as to irradiate the region to be welded. The laser has a control input and is responsive to a control signal supplied to said control input to adjust the power of the beam of laser energy. An infrared sensor senses the temperature of the tissue in the region to be welded by sensing infrared radiation coming from this region. The sensor provides a sensor output indicative of the temperature. A computer control arrangement is responsive to the sensor output. The computer control arrangement supplies a control signal to said laser such that the region to be welded is heated to a predetermined temperature.

13 Claims, 6 Drawing Sheets

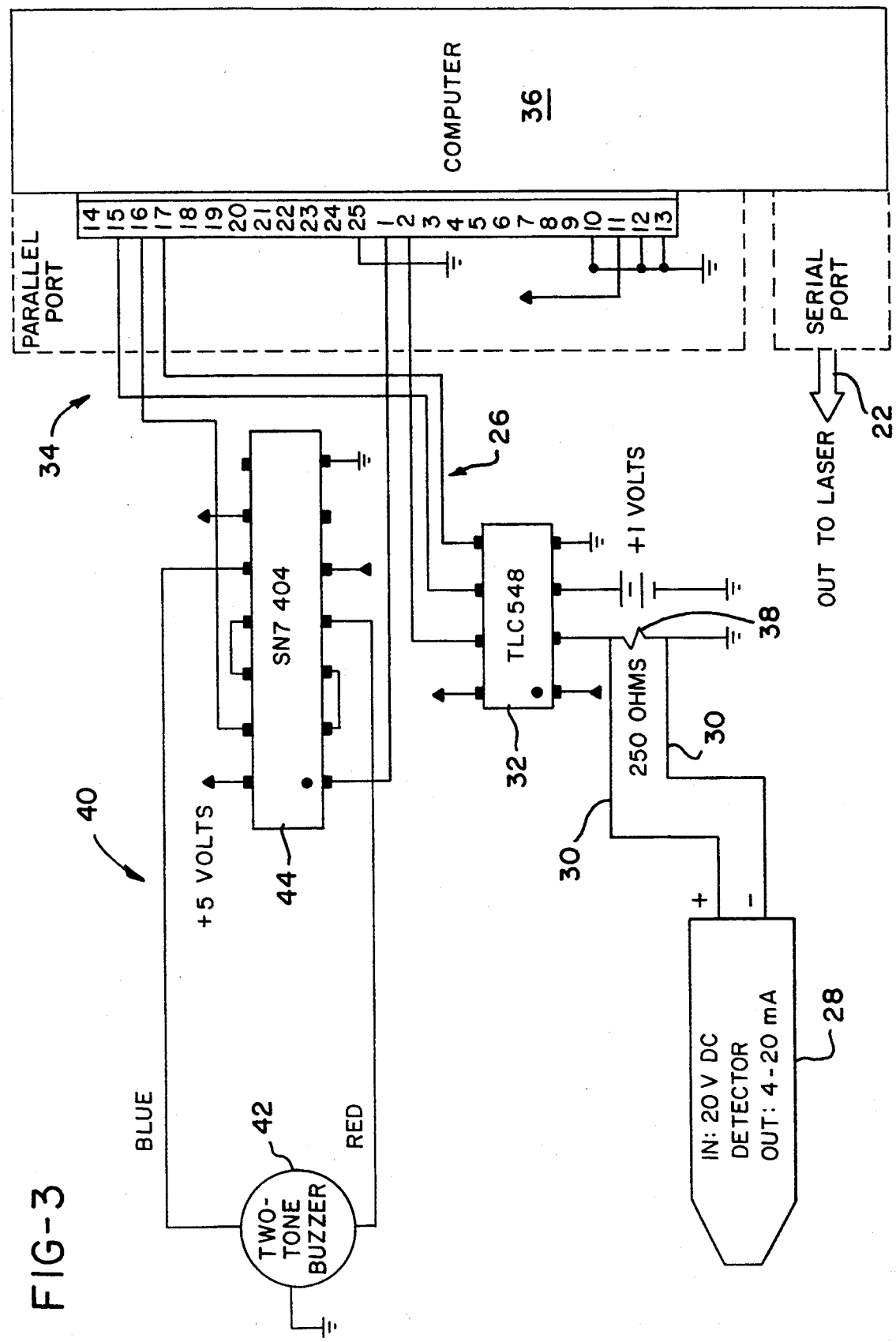

LASER TISSUE WELDING CONTROL SYSTEM

This is a continuation of application Ser. No. 07/88,779, filed May 21, 1992 now U.S. Pat. No. 5,334,191.

BACKGROUND OF THE INVENTION

This invention relates to tissue welding techniques and apparatus for accomplishing tissue welding and, more particularly, to a method and an apparatus by which tissue may be reliably welded under controlled conditions.

Lasers of various types have long been used in various medical applications. In a wide variety of surgical techniques, a beam of laser light is used to cut tissue, and to coagulate along the cut at the same time. Although commonly used for tissue destruction, lasers have not gained the same widespread use for reconstructive procedures. Some progress has previously been made, however, in the use of laser energy for joining tissue, commonly termed tissue welding. The ultimate goal is to facilitate the joining of two tissues with a minimum of scar and good tensile strength of the apposed edges.

The mechanism of tissue welding is complex, and there are many variables that can be adjusted or modified in the welding process. Some evidence suggests that the mechanism of welding may vary depending upon which type of laser is used. Welding of blood vessels with an Nd:YAG laser produces an interdigitation of collagen which is the structural basis of the effect. As such, the collagen fibrils develop a change in periodicity but are still recognizable. Similarly, welding with an argon laser likely involves a structural change in the welded tissues.

In contrast to the argon and Nd:YAG lasers, which penetrate through the tissue, the $CO_2$ laser produces heating with only superficial penetration. As a consequence, the $CO_2$ laser probably accomplishes welding through yet another mechanism. A $CO_2$ laser produces heating at the tissue surface, and this destroys tissue to the extent that a coagulum is produced which seals the edges to be joined. This denaturation of proteins occurs between 60° C. and 70° C.

The success of tissue union is dependent on several factors. First, it is necessary to align the edges of the tissue without tension. Second, a close approximate in the shape of the tissue edges is essential so that the laser energy is equally distributed to both edges. Third, since laser welding will inevitably destroy some of the tissue edge, it is important to have enough tissue so that stricture will not occur. Fourth, an adjustment of laser parameters to minimize peripheral tissue destruction will improve results. A protein solder has also been found to be helpful in minimizing the last two problems, as seen in several reports. Poppas, D., Schlossberg, S., Richmond, I., et al: "LASER WELDING IN URETHRAL SURGERY: IMPROVED RESULTS WITH A PROTEIN SOLDER", *The Journal of Urology*, Vol. 139, February 1988, pages 415–417; and Ganesan, G., Poppas, D., Devine, C.: "URETHRAL RECONSTRUCTION USING THE CARBON DIOXIDE LASER: AN EXPERIMENTAL EVALUATION", *The Journal of Urology*, Vol. 142, October 1989, pages 1139–1141.

In the past, the success of the tissue welding process has clearly been dependent in part upon the skill of the surgeon operating the laser. When lasers are used clinically for destructive purposes, the effect of laser light on the tissue is determined principally by visual observation. Since tissue destruction is the goal, assessing the degree of destruction by visual inspection is a fairly straightforward process. This is especially true of the $CO_2$ laser which has a very short extinction coefficient. When using the Nd:YAG laser, some guidelines are available to help assess the amount of laser energy needed. Since the Nd:YAG laser has a longer extinction coefficient, however, tissue changes at the surface may not always be indicative of the effects that the laser energy has produced deeper in the tissues.

Determining when the end point of the tissue fusion process has been reached merely based on visual observation of the irradiated tissue, as has been done in the past, is less acceptable than using visual observation with destructive procedures. In prior tissue welding techniques, the surgeon has typically observed the tissue as it was irradiated, and when the tissue has changed to a golden brown color, welding is stopped. It will be appreciated, therefore, that the success rate achieved in laser welding techniques has been operator dependent to a significant degree.

It is seen, therefore, that there is a need for an improved method of tissue welding, and for apparatus for effecting this method, in which tissues are joined in an atraumatic, rapid, and reliable fashion.

SUMMARY OF THE INVENTION

This need is met by a system and method according to the present invention for welding tissue by irradiation with laser energy. The system includes laser means for generating a beam of laser energy and directing the beam toward the tissue so as to irradiate the region to be welded. The laser means has a control input and is responsive to a control signal supplied to the control input to adjust the power of the beam of laser energy. The system further includes a sensor means for sensing the temperature of the tissue in the region to be welded and for providing a sensor output indicative of the temperature. Finally, the system incorporates a control means that is responsive to the sensor output for supplying a control signal to the laser means. By this arrangement, the region to be welded is heated to a predetermined temperature, and welding is accomplished in a rapid, reliable manner.

The sensor means may comprise an infrared radiation detector for detecting infrared radiation emanating from the region to be welded. The infrared radiation detector provides an analog signal indicative of the level of infrared radiation sensed. The sensor means comprises an analog to digital converter, responsive to the analog signal from the infrared radiation detector, for the sensor output to the control means as a digital sensor output.

The system may further include an indicator means for indicating to the operator whether the sensed temperature in the region to be welded is higher than, lower than, or equal to the predetermined, desired temperature. The indicator means includes means for generating aural indications of whether the sensed temperature in the region to be welded is higher than, lower than, or equal to the predetermined, desired temperature. The indicator means may provide tones which are characteristic of whether the sensed temperature in the region to be welded is higher than, lower than, or equal to the predetermined temperature.

The tissue in the region to be welded may be coated with a fluorescent solder or other material, such as a fluorescent dye alone. When irradiated with laser energy from the laser means, the fluorescent solder or fluorescent dye fluoresces at a wavelength which differs from the wavelength of the laser energy. When such a solder or dye is utilized, the system may further comprise a means for sensing fluorescence and for providing a safety output signal. The control means is then responsive to the safety output signal so as to terminate operation of the laser means in the event that fluorescence is not sensed. The laser means preferably generates a beam of laser energy at a wavelength of approximately 500 nm to 820 nm, and may include a GaAlAs diode laser emitting a beam of laser energy at a wavelength of approximately 780 nm to 820 nm. The fluorescent solder or fluorescent dye fluoresces in response to irradiation with light of such wavelengths. The dye may preferably comprise an exogenous dye, such as for example indocyanine green.

The control means may comprise a programmed digital computer.

The laser means for generating a beam of laser energy and directing the beam toward the tissue so as to irradiate the region to be welded includes a laser source for generating the laser beam, and a fiber optic conductor for directing the beam toward the tissue to be welded. The fiber optic conductor may comprise a single optical fiber for directing the beam toward the tissue so as to irradiate the region to be welded and for returning infrared radiation to the infrared radiation detector from the region to be welded. Alternatively, the fiber optic conductor may comprise at least one optical fiber for directing the beam toward the tissue so as to irradiate the region to be welded, and at least one optical fiber for directing the infrared radiation emanating from the region to be welded to the sensor means for sensing the temperature of the tissue in the region to be welded and for providing a sensor output indicative of the temperature.

A method for welding tissue by irradiation with laser energy according to the present invention, comprises the steps of:

a) generating a beam of laser energy,
b) directing the beam of laser energy toward the tissue so as to irradiate the region to be welded,
c) sensing the temperature of the tissue in the region to be welded, and
d) adjusting the power of the beam of laser energy such that the region to be welded is heated to a predetermined temperature.

The step of sensing the temperature of the tissue in the region to be welded may comprise the step of detecting infrared radiation emanating from the region to be welded and determining the temperature based upon the level of the infrared radiation.

The method may further includes the steps of:

a) coating the tissue in the region to be welded with a solder or other material which, when irradiated with the laser energy, fluoresces at a wavelength which differs from the wavelength of the laser energy,
b) sensing fluorescence, and
c) automatically terminating irradiation of the region to be welded with laser energy in the event that fluorescence is not sensed.

Accordingly, it is an object of the present invention to provide an improved system and method for welding tissue in which the tissue in the region to be welded is irradiated with laser radiation and is maintained at a predetermined temperature; to provide such a system and method in which the temperature of the tissue in the region to be welded is sensed by means of an infrared sensor; to provide such a system and method in which a computer based control is responsive to the output of the infrared sensor for automatically controlling the temperature of the tissue in the region to be welded; and to provide such a system and method in which the region to be welded is coated with a solder or dye material which fluoresces, and in which the system includes a sensor for detecting the fluorescence.

Other objects and advantages of the invention will be apparent from the following description, the accompanying drawings and the appended claims.

BRIEF DESCRIPTION OF THE DRAWINGS

FIG. 3 is a more detailed schematic representation of a portion of the system of FIGS. 1 and 2;

DETAILED DESCRIPTION OF THE PREFERRED EMBODIMENTS

Controlling the application of laser energy to tissue to effect a bond or weld has been something of an art. The amount of such energy applied to tissue has been based in large part upon a subjective analysis of visually perceivable changes in the appearance of the tissue surface, with the result that variations in welding effectiveness occurred. It has been found that weld bonding strength is affected by laser parameters, such as power and exposure, and that these parameters directly determine surface temperature. It is believed that maintaining tissue at a constant temperature during welding produces uniform bonding with a minimum of tissue damage. As a consequence, the present invention incorporates a control system that enables the surgeon to maintain relatively specific tissue temperatures for the purpose of laser welding.

Figure 1:
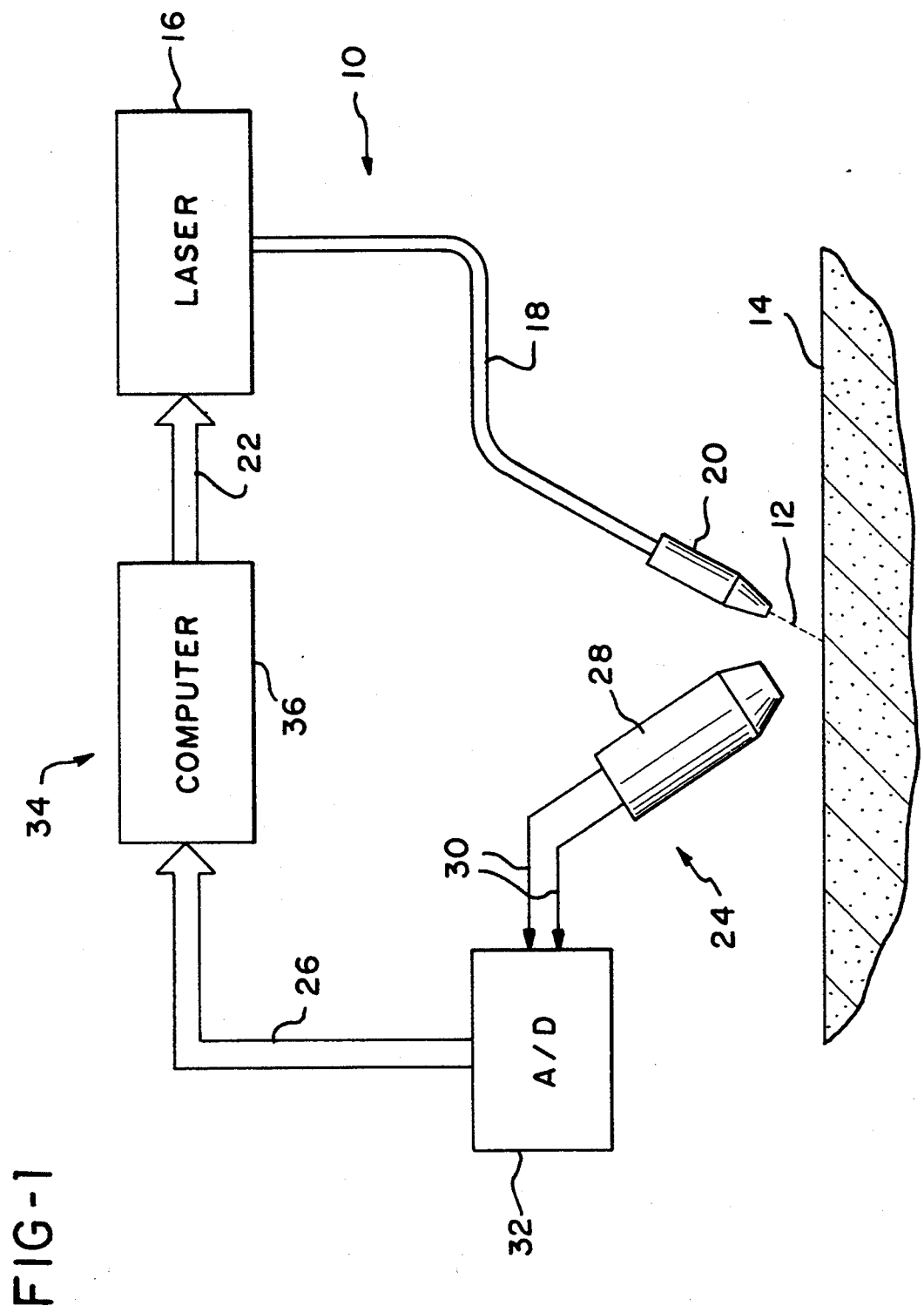
FIG. 1 is a schematic representation of the system for welding tissue by irradiation with laser energy according to one embodiment of the present invention.

FIG. 1 illustrates schematically a first embodiment of a system for welding tissue by irradiation with laser energy, constructed according to the present invention. The system includes laser means 10 for generating a beam of laser energy 12 and directing the beam toward the tissue 14 so as to irradiate the region to be welded. The laser means 10 includes a laser source 16 for generating the laser beam, and a fiber optic conductor 18 extending through a handpiece 20 for directing the beam toward the tissue 14. The laser source 16 may comprise any one of a number of commercially available laser devices, such as for example a Laserscope 803 Nd:YAG/KTP laser having an RS-232 communications port, manufactured by Laserscope Corporation, San Jose, Calif. The laser source 16 has a control input 22, and is responsive to a control signal supplied to the control input 22, to adjust the power of the beam 12 of laser energy. Power adjustment can be effected in any one of a number of ways. Preferably, however, the laser beam 12 is pulse width or duty cycle modulated to vary the average power of the beam.

The system includes a sensor means 24 for sensing the temperature of the tissue 14 in the region to be welded and for providing a sensor output on 26, indicative of the sensed temperature. The sensor means 24 includes an infrared radiation detector 28 for detecting infrared radiation emanating from the region to be welded. As is known, the amplitude of the infrared radiation emanating from the surface of an object is proportional to the temperature of the object.

The infrared wavelength range to which the detector 28 is responsive is selected to differ from the wavelength of the laser beam 12. Thus, any direct reflection of the beam 12 from the tissue to the sensor is prevented from altering the temperature measurements made by sensor 28.

The infrared radiation detector 28 provides an analog signal 30 indicative of the level of infrared radiation sensed. The sensor means 24 further comprises an analog to digital converter 32, responsive to the analog signal from the infrared radiation detector 28, for providing a sensor output 26 in digital form. The infrared detector may preferably be a Model M67S, produced by Mikron Instrument Co., Inc., Wyckoff, N.J. This detector is a pyrometer that accepts infrared wavelengths in the 8 to 14 micron range of the electromagnetic spectrum proportional to the temperature of the viewed object in the range 0° F. to 500° F. (−17° C. to 273° C.). The detector 28 operates on a 20 volt d.c. power supply, and provides an output of 4–20 ma. d.c. that varies linearly with the temperature. The detector 28 is positioned approximately 2 inches above the surface of the operative field at an angle of 20° from vertical. If desired or necessary, the signal-to-noise ratio of the detector output may be enhanced by providing a shutter mechanism for alternately blocking infrared radiation from reaching the detector 28, and permitting it to reach detector 28. The sensor output 26 will then alternate between a level reflecting ambient temperature and a level associated with tissue temperature, enhancing detector sensitivity.

The system further includes a control means 34, responsive to the sensor output 26, for supplying a control signal on control input 22 to the laser means 10 such that the region to be welded is heated to a predetermined temperature or maintained within a predetermined temperature range. The control means 34 preferably comprises a programmed digital computer 36, such as for example an IBM PS/2 Model 50 Z personal computer. Computer 36 operates under the control of appropriate software. An example of such software is a listing of source code, to be interpreted on a Microsoft ® Quick C software compiler, which is included as an appendix hereto.

A more detailed schematic of a portion of the system of the present invention is illustrated in FIG. 3. The infrared radiation detector 28 supplies a current output across resistor 38, converting the output to an electrical potential which is the input to analog to digital converter 32. Converter 32 is preferably a serial 8-bit A/D converter that accepts voltages generated by the detector 28, and provides one of 256 digitized values to the parallel port of the IBM PS/2 computer 36. The computer 36 then controls the operation of the laser 16 (FIG. 1) via its serial port.

The system further includes an indicator means 40 for indicating to the surgeon whether the sensed temperature in the region to be welded is higher than, lower than, or equal to a predetermined temperature or temperature range. The indicator means includes a two-tone buzzer 42, driven by circuit 44, under control of computer 36. The buzzer 42 generates aural indications of whether the sensed temperature in the region to be welded is higher than, lower than, or equal to the predetermined temperature. When the sensed temperature is less than the predetermined temperature, no tone is produced. When the sensed temperature is higher than the predetermined temperature, a high tone is generated. When the sensed temperature is the same as the predetermined temperature, a low tone is generated. Circuit 44 preferably includes integrated circuit S.N.7404 which powers the two-tone buzzer 42.

The control system of the present invention enables the surgeon to maintain specific tissue temperatures for the purpose of laser welding. The temperature sensing component is capable of measuring tissue temperatures to within ±1.2° C. when compared to a calibrated J type thermocouple mounted on a 30 gauge hypodermic needle. The system is able to obtain the desired surface temperature in an average of 6.3 seconds by intermittent power adjustments up or down from a baseline of 100 mw. Once the desired temperature is attained, the control system contains overshoot to within +4° C. After the system has reached equilibrium, temperature measurements are held to within ±2° C. of the desired temperature.

Information from the analog to digital converter 32 is processed by computer 36 as continuous, real time temperature measurements. The computer 36 compares the current temperature of the tissue in the region to be welded to a desired temperature value previously entered by the surgeon. Depending upon the difference between these two values, the computer 36 adjusts the current power setting of the laser to maintain the desired surface temperature.

The computer 36 may cause the energy of beam 12 to be adjusted in any one of a number of ways. One technique for altering the energy of beam 12 is to modulate it in a duty cycle fashion. With duty cycle modulation, the beam is on for varying percentages of each cycle, thus permitting a significant range of power settings.

Figure 2:
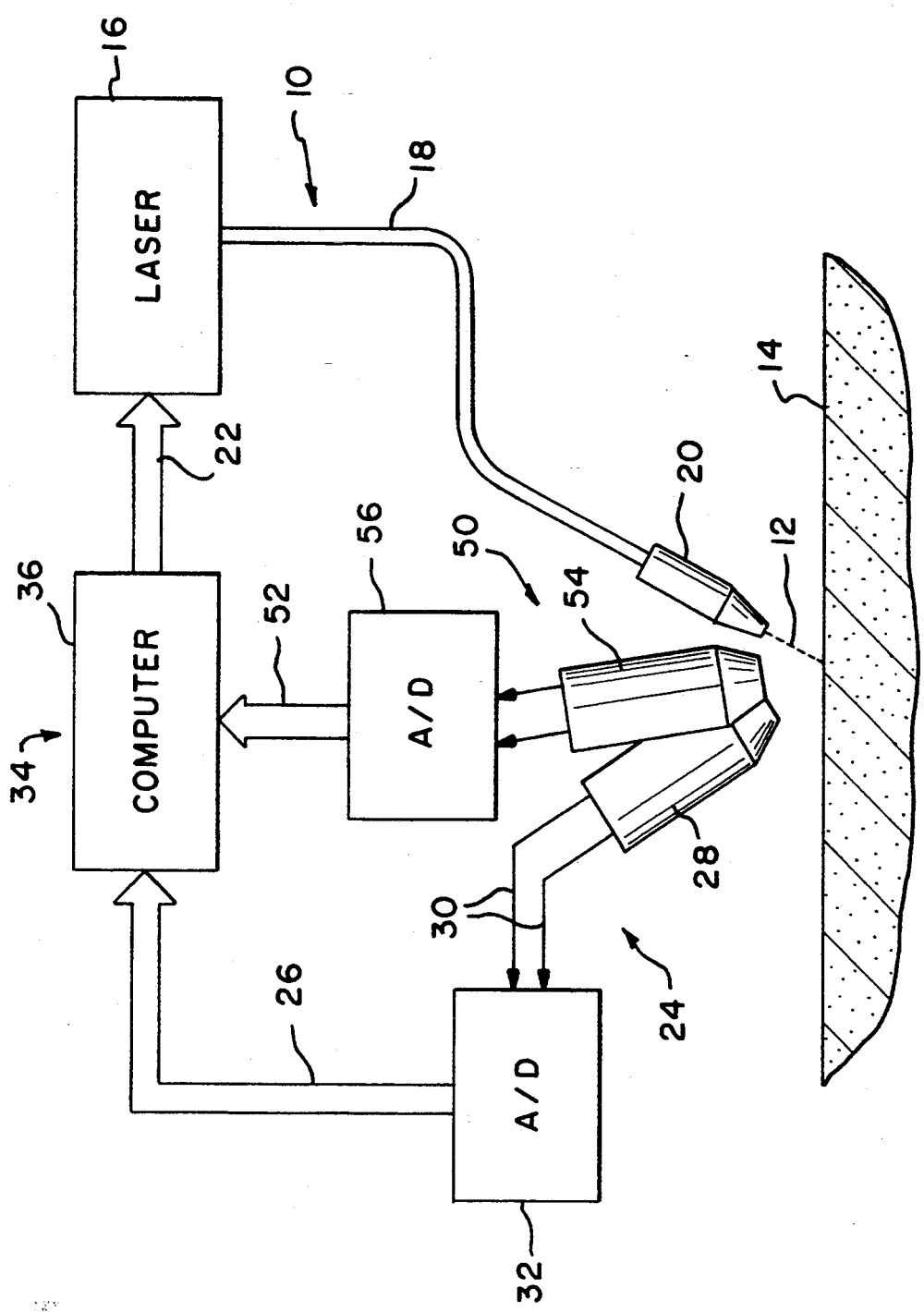
FIG. 2 is a schematic representation of another embodiment of the system for welding tissue by irradiation with laser energy according to the present invention.

FIG. 2 illustrates a second embodiment of the present invention. Many of the components of the embodiment of FIG. 2 are the same as those of the embodiment of FIG. 1. For simplicity of explanation, common components have been given the same reference numerals in both drawings, and will not be 10 separately described with respect to FIG. 2. As is known, the use of a solder material has been found to facilitate the welding process. It has also been found that some solder materials or other materials such as dyes will fluoresce, either at a visible light wavelength or otherwise, in response to being irradiated with a laser beam. The embodiment of FIG. 2 takes advantage of this effect. With this embodiment, just the tissue in the region to be welded is coated with a solder or other material, such as a dye, which fluoresces when irradiated with laser energy from the laser means 10. This fluorescence occurs at a wavelength which differs from the wavelength of the laser light in beam 12.

The system includes a means 50 for sensing fluorescence by the solder and for providing a safety output signal on 52 to the computer 36. Means 50 includes a detector 54 and an analog to digital converter 56 of the same general type as detector 26 and analog to digital converter 32, respectively. Detector 54, however, is selective, responding only to energy having a wavelength approximating that of the expected fluorescence. The control means 34 is responsive to the safety output signal on 52 so as to terminate operation of the laser 16 in the event that fluorescence is not sensed.

Thus, if the beam 12 is properly aimed, irradiating the solder, fluorescence will be sensed. If, however, means 50 ceases to sense fluorescence, this is an indication that the beam is improperly aimed. This condition will be quickly alleviated, as the computer 36 will immediately terminate operation of laser 16. It will be appreciated that materials fluoresce at wavelengths that differ from the wavelengths of the energy that produces the fluorescence. As a consequence, means 50 is selected to respond to a range of wavelengths which does not encompass the wavelength of beam 12, such that its readings will not be affected by direct reflection of beam 12.

Figure 4A:
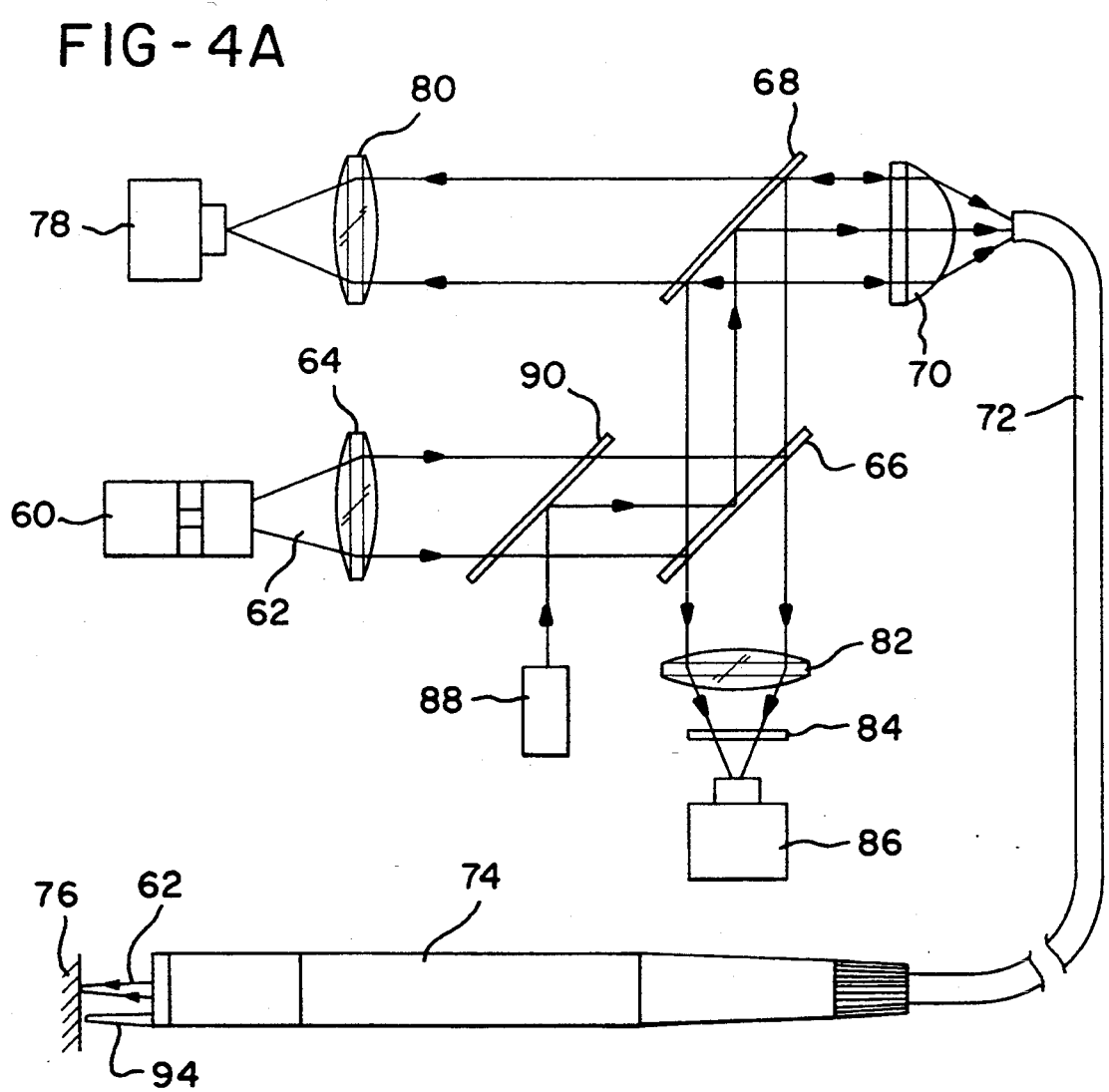
FIG. 4A is a schematic representation of another embodiment of the system for welding tissue by irradiation with laser energy, directing the laser energy and monitoring its application through a single optical fiber.
Figure 4B:
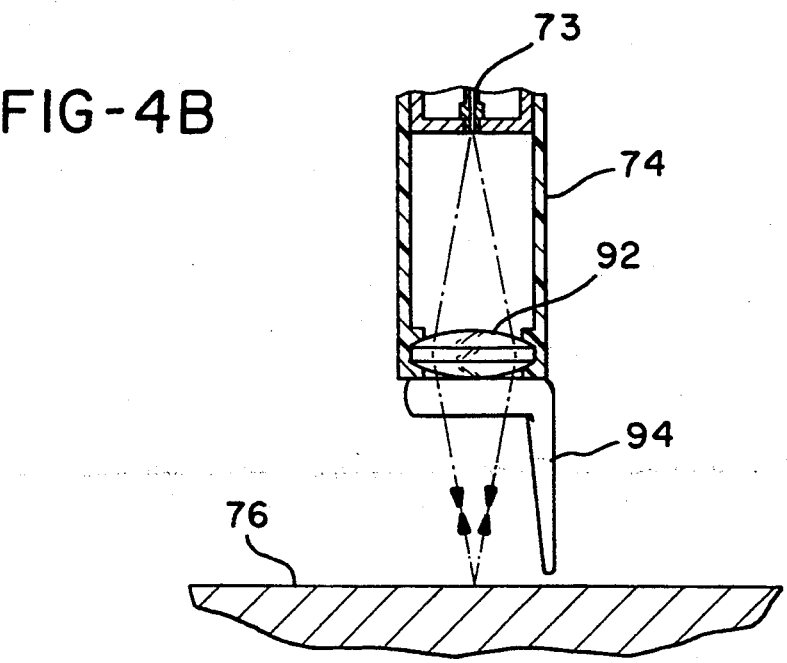
FIG. 4B is a partial axial sectional view, illustrating the end of the handpiece of the system of FIG. 4A.

Reference is now made to FIGS. 4A and 4B, which illustrate another embodiment of the present invention, similar in some respects to that shown in FIG. 2, in that fluorescence of a fluorophore dye material, or other material capable of fluorescence, is monitored, as is the temperature of the tissue through measurement of infrared radiation. The embodiment includes a laser source 60 which may, for example, comprise a GaAlAs diode laser that emits a beam of laser energy 62 at a wavelength of approximately 780 nm to 820 nm. It will be appreciated that other laser sources, preferably providing energy at a wavelength between 500 nm and 820 nm, may be utilized. The beam is collimated by lens 64, reflected by optical beam splitters 66 and 68, and focused by lens 70, coupling the beam into a fiber optic conductor 72 carrying a single optical fiber 73 (FIG. 4B). Fiber optic conductor 72 directs the laser beam 62 through a handpiece 74 to the tissue 76 which is to be welded. Infrared radiation from tissue 76 is monitored by temperature detector 78 which receives the infrared radiation via the fiber optic conductor 72. Lens 70 collimates the infrared radiation, which then passes through beamsplitter 68 and is focused by lens 80.

It will be appreciated that the wavelength of the returning infrared radiation is in the 2 $\mu$m to 20 $\mu$m range. The laser beam, however, has a wavelength of 780 nm to 820 nm. As a consequence, the optical fiber 73 in fiber optic conductor 72 must be able to transmit energy at both of these wavelengths. It has been found that an optic fiber made of a fluoride glass meets these criteria.

Such an optic fiber is also capable of transmitting light produced by the fluorescing of the solder. With a GaAlAs diode laser emitting light at approximately 780 nm to 820 nm, and illuminating an exogenous dye, indocyanine green (ICG), fluorescence at a wavelength of approximately 0.85 $\mu$m is produced. This light returns along the fiber optic conductor 72, is collimated by the lens 70, is reflected by the beamsplitter 68, and passes through beamsplitter 66. The light from the fluorescence of the ICG dye is then focused by lens 82 and directed through filter 84 to detector 86. Filter 84 is a bandpass filter that passes only light in the fluorescence range, approximately 0.85 $\mu$m, to detector 86. Detector 86 may consist of a simple diode detector.

An aim source 88 provides a low power visible beam to indicate the optical path of the treatment beam and facilitate aiming of the treatment beam by the surgeon. Preferably, the aim source is a visible diode laser operating in the 400 nm to 700 nm wavelength range, or a super-radiant LED.

The use of a single optical fiber 73 for delivering the treatment beam and the aiming beam to the tissue and returning the infrared radiation and the fluorescent light to the system provides a number of advantages. In addition to its simplicity of construction, this arrangement insures that the infrared radiation being measured emanates from the area being irradiated with laser light.

FIG. 4B shows the distal end of the handpiece 74, with portions in section. The beam 62 emerges from the end of the single optical fiber 73 and is focused by lens 92 at a distance of approximately 25 mm. In order to assist the surgeon in properly positioning the handpiece 74, a guide 94 of approximately 25 mm length, is mounted on the end of the handpiece 74. If the guide 94 is in contact with the tissue, or nearly so, the beam of laser energy will be properly focused on the tissue.

Figure 5:
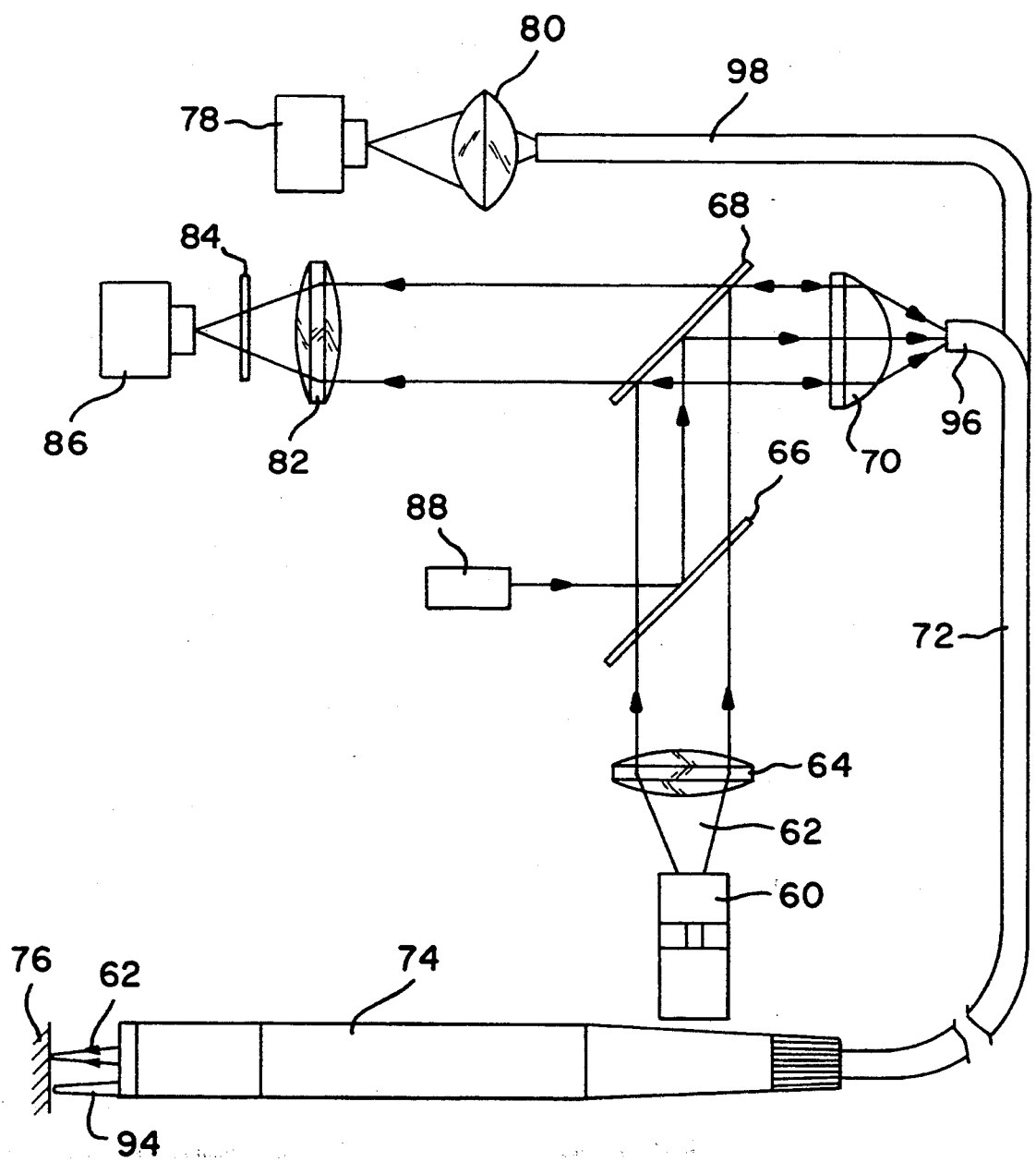
FIG. 5 is a schematic representation of another embodiment of the system for welding tissue by irradiation with laser energy, directing the laser energy and monitoring its application through separate fibers in a fiber optic bundle.

In contrast to the embodiment of FIG. 4A, FIG. 5 illustrates an embodiment of the present invention, in which separate optical fibers are provided for the transmission of laser energy to the tissue and the return of infrared radiation and light produced by the fluorescence of the solder. In most respects the embodiment of FIG. 5 is the same as that shown in FIG. 4, and identical reference numerals have been used in FIG. 5 to identify corresponding elements.

In the system of FIG. 5, the fiber optic conductor 72 comprises at least one optical fiber in conductor portion 96 for directing the beam toward the tissue so as to irradiate the region to be welded. The conductor 72 further comprises at least one optical fiber in conductor portion 98 for directing the infrared radiation emanating from the region to be welded to the temperature sensor 78. Temperature sensor 78 provides a sensor output indicative of the temperature of the tissue being welded in the manner described previously. The optical fiber in portion 96 is preferably silica glass, whereas the optical fiber in portion 98 is an infrared transmitting fiber such as a fluoride or chalcogenide glass which transmits the infrared radiation wavelengths to which sensor 78 responds.

It will be appreciated that the embodiment of FIG. 5 requires at least one additional optical fiber, as compared to the embodiment of FIG. 4A. However, the embodiment of FIG. 5 does not include a beamsplitter in the optical path of the infrared radiation returning to the infrared sensor 78, thereby eliminating any attenuation that might otherwise occur as a result of the presence of such a beamsplitter in the optical path. One difficulty with this arrangement, however, is that the region of the tissue from which the infrared radiation is received may not be precisely the same area that is irradiated with the laser beam.

Figure 6:
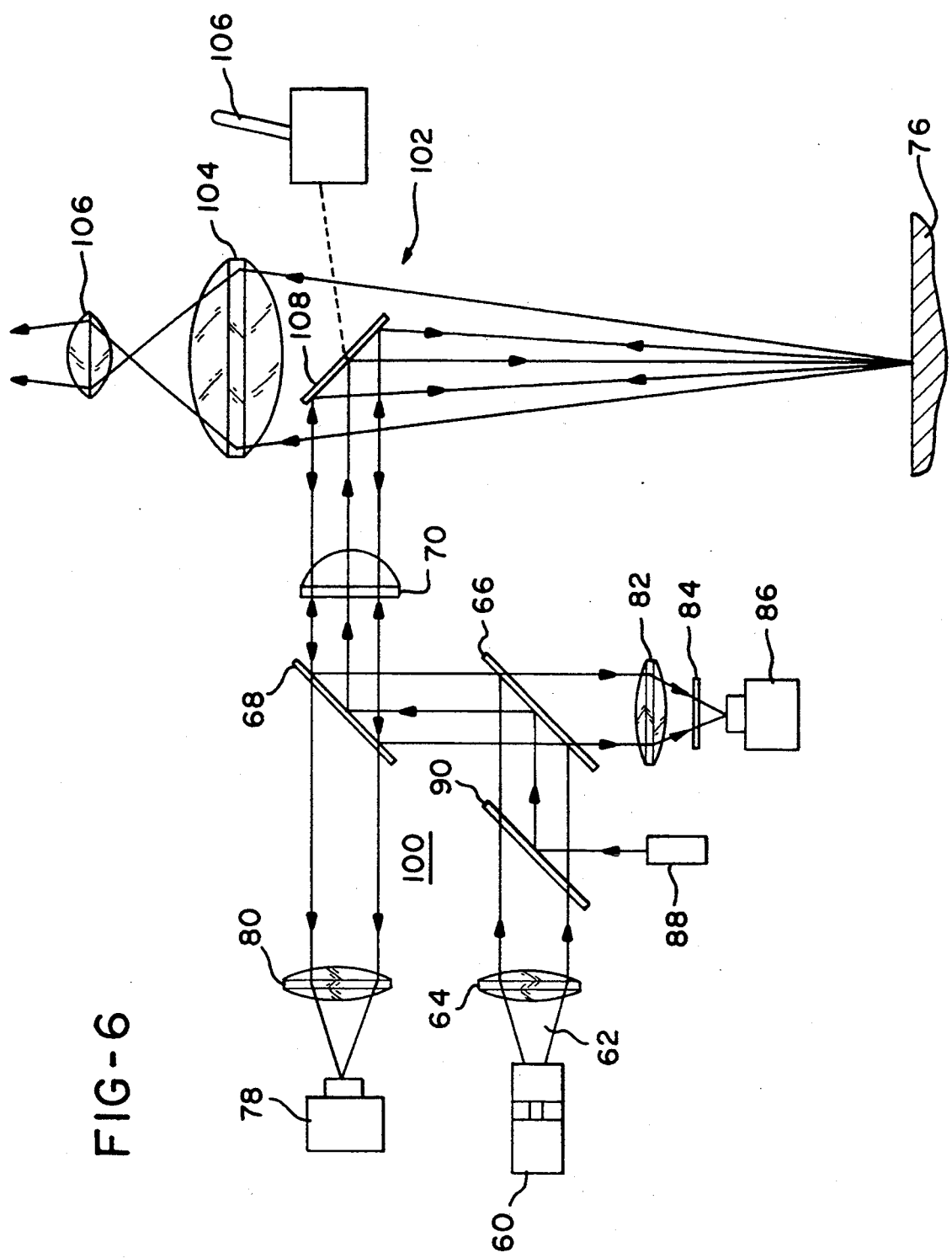
FIG. 6 is a schematic representation of another embodiment of the system for welding tissue by irradiation with laser energy, directing the laser energy and monitoring its application through a surgical microscope.

Reference is now made to FIG. 6, which illustrates the principles of operation of the present invention in a surgical microscope. The system of FIG. 6 includes means 100 for generating a laser beam, and for detecting fluorescent light and infrared energy, which are the same as those described in connection with FIG. 4A, and which bear the same reference numerals. Rather than cooperating with a fiber optic conductor and a handpiece, the means 100 for generating a laser beam, and for detecting fluorescent light and infrared energy is operated in conjunction with a surgical microscope 102, which includes lenses 104 and 106, for viewing the tissue 76 during welding. Microscope 102 includes a mirror 108, the orientation of which can be controlled by a joystick micromanipulator 106 to precisely adjust the position of the target beams within the viewing field of the microscope 102.

It should be appreciated that further variations can be made in the system of the present invention, including the addition to an endoscope of a means for generating a laser beam, and for detecting fluorescent light and infrared energy in accordance with the present invention. With such an arrangement, the endoscope is modified to include a port for an optical fiber or other optics to integrate the laser generation and detection arrangement described above into the endoscope.

Having described the invention in detail and by reference to the preferred embodiments thereof, it will be apparent that other modifications and variations are possible without departing from the scope of the invention defined in the appended claims.

Source code interpreted on Microsoft Quick C software compiler.

```
#include <graph.h>
#include <stdio.h>
#include <time.h>
#include <conio.h>
#include <ctype.h>
#include <bios.h>
include <stdlib.h> define RED 4
define BLUE 9
#define WHITE 15
#define BLACK 0
#define YELLOW 14
#define OFF 9
#define ON 8
#define ON2 12
#define PORT_1 957
#define CS_PORT 958
#define IO_PORT 956
#define COM1 0
define STATUS 0x100 int enter_val, light, max_val, count, power, temp_point[3000], power_point[3000];
unsigned int portv(), calibrate(), review_data(), draw_graph(), laser_loop(int test_point);
float red_rect(float pass_temp);
FILE *infile, *outfile;
int leave(), nextscreen(int first_point), write_tempF, write_temp, integ_temp;
int too_powerful;

main()
{
    char buffer[3], in_char;
    int i, j, enter_val1, enter_valF, c=0, cmax_val;
    unsigned int port_value, data;
    float old_current_temp, current_temp, current_tempred;

outp(CS_PORT,1);   /* TURNS OFF BUZZER */ if (_setvideomode(_VRES16COLOR) == 0)
    {
        /* ERROR SETTING MODE */
        _clearscreen(_GCLEARSCREEN);
        printf ("MODE NOT SUPPORTED BY HARDWARE\n");
```

```
     exit(0);
   }
_clearscreen(_GCLEARSCREEN);
_setbkcolor(_GREEN);
_settextposition(6,15);
infile = fopen("c:\\cb.cb", "r+");
fscanf(infile, "%d", &max_val);
rewind(infile);

/* SETTING UP LASER */
data = (_COM_CHR8 | _COM_STOP1 | _COM_NOPARITY | _COM_9600);
_bios_serialcom(_COM_INIT, COM1, data);

printf("DO YOU WISH TO CALIBRATE ('y' OR 'n')? ");
in_char = getche();
if(in_char == 'y' || in_char == 'Y')
   {
     max_val = calibrate();
   }

_clearscreen(_GCLEARSCREEN);
_setbkcolor(_GREEN);
_settextposition(0,0);
TOP: printf("ENTER THE OPTIMAL BONDING TEMPERATURE (in Celsius): ");
enter_val = 0;
KLIOZE: scanf("%d",&enter_val);
     if (enter_val==0) goto KLIOZE;
enter_val1 = enter_val-25;
_clearscreen(_GCLEARSCREEN);
_setbkcolor(_BLACK);

FIRSTSCREEN:  _settextposition(9,17);
  sprintf(buffer,"%d",enter_val);
  _settextcolor(BLUE);
  _outtext(buffer);
  enter_valF = (enter_val*(9./5.))+32;
  _settextposition(9,62);
  sprintf(buffer,"%d",enter_valF);
  _outtext(buffer);

_settextcolor(WHITE);
  _settextposition(13,33);
  _outtext("0");
  _settextposition(13,45);
  _outtext("0");

_settextposition(10,45);
  sprintf(buffer,"%d", max_val);
  _outtext(buffer);
  cmax_val = (max_val-32)*(5./9.);
  _settextposition(10,32);
  sprintf(buffer,"%d", cmax_val);
  _outtext(buffer);

for(i=0; i<76; i+=5)
   {
     _settextposition(26,i+1);

if (i == enter_val1)
```

```
{
 _settextcolor(BLUE);
 _outtext("|");
 _settextposition(27,i+1);
 sprintf(buffer,"%d",i+25);
 _outtext(buffer);
 _settextcolor(WHITE);

goto NEXT1;
 }
 _outtext("|");
 _settextposition(27,i+1);
 sprintf(buffer,"%d",i+25);
 _outtext(buffer);

NEXT1: if(i == 75) goto NEXT2;

for(j=1; j<5; j++)
 {
  _settextposition(26, i+j+1);
  if(i+j == enter_val1)
 {
  _settextcolor(BLUE);
  _outtext (".");
  _settextcolor(WHITE);
  goto NEXT2;
 }
 _outtext(".");

NEXT2: _asm nop
 }
}
 old_current_temp = 0;

/******************************************/
 _setcolor(10);
 _rectangle(_GBORDER,40,100,240,250);
 _rectangle(_GBORDER,400,100,600,250);
 _rectangle(_GBORDER,240,125,400,170);
 _rectangle(_GBORDER,240,180,400,225);

_settextcolor(12);
 _settextposition(11,10);
 _outtext("DEGREES CELSIUS");
 _settextposition(11,55);
 _outtext("DEGREES FAHRENHEIT");
 _settextposition(10,37);
 _outtext("maximum");
 _settextposition(13,38);
 _outtext("timer");

/******************************************/

GO: if( kbhit())
 {
  c = getch();
  if(c==27) leave();
  if(c==8)
```

```
      {
        nextscreen(current_temp);
        _clearscreen(_GCLEARSCREEN);
        goto FIRSTSCREEN;
      }
      _clearscreen(_GCLEARSCREEN);
      goto TOP;
    } light = OFF;
    port_value = portv();
    current_temp = ((port_value) /(255.)) * max_val;
    current_temp = (current_temp-32)*(5./9.);
    if (current_temp < old_current_temp)
    {
      old_current_temp = current_temp;
      write_temp = current_temp; /* TEMPERATURE WRITTEN TO SCREEN */
      write_tempF = (write_temp*(9./5.))+32;
      integ_temp=((current_temp-25) * 600.)/75.;

_settextcolor(WHITE);
      _settextposition(13, 17);
      sprintf(buffer,"%d ",write_temp);
      _outtext(buffer);
      _settextposition(13,62);
      sprintf(buffer,"%d ",write_tempF);
      _outtext(buffer);

_setcolor(BLACK);
      _rectangle(_GFILLINTERIOR, integ_temp, 360, 640 ,400);
      goto GO;
    } if(current_temp >= enter_val-1)
    {
      current_tempred = current_temp;
      current_temp = red_rect(current_tempred);
      if(current_temp == -1) goto TOP;
    } old_current_temp = current_temp;
    write_temp = current_temp;
    write_tempF = (write_temp*(9./5.))+32;
    integ_temp=((current_temp-25) * 600.)/75.;

_settextcolor(WHITE);
      _settextposition( 13, 17);
      sprintf(buffer,"%d ", write_temp);
      _outtext(buffer);
      _settextposition(13,62);
      sprintf(buffer,"%d ", write_tempF);
      _outtext(buffer);

_setcolor(WHITE);
      _rectangle(_GFILLINTERIOR, 0, 360, integ_temp, 400);
      goto GO;
  }
```

```
unsigned int portv()
  {
    int i, totalave=0, count;
    unsigned int p_value, new_port;

count = 1;
LOOP: outp(IO_PORT,1);
    outp(CS_PORT,light);
    new_port=0;

_asm nop p_value = inp(PORT_1);
    p_value = p_value >> 3;
    p_value = p_value & 1;
    new_port = new_port | p_value;

for(i=0; i<7; i++)
      {
        outp(IO_PORT,0);
        p_value = inp(PORT_1);
        p_value = p_value >> 3;
        p_value = p_value & 1;
        outp(IO_PORT,1);

new_port = new_port <<1;
        new_port = new_port | p_value;
      } outp(CS_PORT,light-8);
      totalave = totalave + new_port;
      count = count + 1;
      if ( count > 100)
        {
        new_port = totalave/100.;
        return(new_port);
        }
      goto LOOP;

} float red_rect( float pass_temp)
  {
    char buffer[3];
    double tused;
    unsigned int port_value, color, color2;
    float old_current_temp;
    time_t tstart, tstop;
    int ipass;

time(&tstart);

FLY: if(kbhit())
    {
      pass_temp = -1;
      _clearscreen(_GCLEARSCREEN);
      return( pass_temp);
    }
    ipass = pass_temp;
    if(ipass >= enter_val-1 && ipass <= enter_val+1)
```

```
        light = ON;
else
        light = ON2;

old_current_temp = pass_temp;
    write_temp = pass_temp;
    write_tempF = (write_temp*(9/5.))+32;
    integ_temp = ((pass_temp - 25) * 600)/75.;

_settextcolor(BLUE);
    _settextposition(13,17);
    sprintf(buffer, "%d ", write_temp);
    _outtext (buffer);
    _settextposition(13,62);
    sprintf(buffer, "%d ", write_tempF);
    _outtext(buffer);

_settextcolor(YELLOW);
    _settextposition(13,33);

time(&tstop);
    tused = difftime(tstop,tstart);
    sprintf(buffer, "%g ", tused);
    _outtext(buffer);
    _settextposition(13,45);
    _outtext(buffer);

_setcolor(RED);
    _rectangle(_GFILLINTERIOR, 0, 360, integ_temp, 400);

PASSAGE: port_value = portv();
    pass_temp = ((port_value) /(255.)) * max_val;
    pass_temp = (pass_temp-32)*(5/9.);
    ipass = pass_temp;
    if (pass_temp >= old_current_temp) goto FLY;

if (ipass < enter_val -1)
   {
    color = WHITE;
    color2 = WHITE;
    goto START;
   }
  color = YELLOW;
  color2 = BLUE;
  if(ipass >= enter_val-1 && ipass <= enter_val+1)
      light = ON;
  else
      light = ON2;

START: integ_temp = ((pass_temp -25)* 600)/ 75.;
    old_current_temp = pass_temp;
    write_temp = pass_temp;
    write_tempF = (write_temp*(9/5.))+32;
    time(&tstop);
    tused = difftime(tstop,tstart);   /* STOP TIMER IF EXITING */
    _settextcolor(color);
    _settextposition(13,33);
    sprintf( buffer,"%g ", tused);
    _outtext(buffer);
    _settextposition(13,45);
```

```c
        _outtext(buffer);

_settextcolor(color2);
    _settextposition(13, 17);
    sprintf( buffer, "%d ", write_temp);   /* CHANGE OUT COLOR */
    _outtext(buffer);
    _settextposition(13,62);
    sprintf(buffer, "%d ", write_tempF);
    _outtext(buffer);

_setcolor(BLACK);
    _rectangle(_GFILLINTERIOR, integ_temp, 360, 640, 400);

if (ipass < enter_val-1) return(pass_temp);

goto PASSAGE;

} unsigned int calibrate()
{
    char outline[40], in_char;
    int i,j, write_temp, enter_temp;
    unsigned int port_value;

light = OFF;
    _clearscreen(_GCLEARSCREEN);
    _setbkcolor(_BLUE);

_settextcolor(RED);

_setcolor(BLUE);
    _rectangle(_GFILLINTERIOR, 100,170,540,245);
    _settextposition(12,24);
    printf("I ASSUME THIS TEMPERATURE IS ");
    _settextposition(13,25);
    printf("                              ");
    _settextposition(14,25);
    printf("HIT 'RETURN' TO EXIT CALIBRATION");
    _settextposition(15,25);
    printf("  HIT 'SPACE-BAR' TO CALIBRATE  ");

HEY: if(kbhit()) goto LEAVE;
    _settextposition(12,53);
    port_value = portv();
    write_temp= ((port_value )/(255.)) * max_val;
    write_temp= (write_temp-32)*(5/9.);
    sprintf(outline, "%d   ",write_temp);
    _outtext(outline);
    goto HEY;
LEAVE: _clearscreen(_GCLEARSCREEN);
        _setbkcolor(_LIGHTYELLOW);

if((in_char = getch()) == '\r') return(max_val);
    _settextposition(8,25);
    printf("ENTER CALIBRATED VALUE (in Celsius): ");
    scanf("%d",&enter_temp);

enter_temp = (enter_temp*(9/5.))+32;  /* convert C to F */
```

```
    max_val = (enter_temp*255.)/(port_value);
    fprintf(infile,"%d",max_val);
    rewind(infile);
    return(max_val);

} int leave()
 {
  _setvideomode(_DEFAULTMODE);
  exit(0);
 } int nextscreen(int first_point)
 {
  int i, pointnow, pointnow2, pointpast, port_value, c=0, lasing=0, power_graph, last_powerpoint, tf;
  char buffer[80], filename[20], drive[30];
  unsigned status, byte_sent=0;

strcpy(drive, "c:\\laser\\");
  draw_graph();

if(first_point>=101) first_point = 100;
  if(first_point<=29) first_point = 30;
  pointpast=pointnow=(459-(459*((first_point-30)/70.)))+1;

BOOM: _setcolor(0);
     _moveto(31,474);
     _lineto(31,1);

for(i=32; i<=585; i++)
       {
        _setcolor(14);
        _settextposition(2,7);
        sprintf(buffer,"%d  ",power);
        _outtext(buffer);
        _setcolor(0);
        _moveto(i,474);
        _lineto(i,1);

_setcolor(14);
        port_value=portv();

pointnow=((max_val*(port_value/255.))-32)*(5/9.);
        pointnow2 = pointnow;
        _settextposition(2,69);
        sprintf(buffer," %d  ",pointnow);
        _outtext(buffer);
/****************************************************************/
        if(pointnow >= enter_val-1 && pointnow <= enter_val+1 ) light=ON;
        if(pointnow < enter_val-1) light=OFF;
        if(pointnow > enter_val+1) light=ON2;
/****************************************************************/

GOON: if(pointnow >= 101) pointnow=100;
           if(pointnow <= 29) pointnow=30;
           pointnow=(459-(459*((pointnow-30)/70.)))+1;

_setcolor(10);
```

```c
_moveto(i-1,pointpast);
_lineto(i,pointnow);
pointpast=pointnow;

if(kbhit())
    {
        c=getch();
        if(c==8) return;
    }
/**************************************************************************/
/* CHECK TO SEE IF LASER HAS ENTERED LASING LOOP (IS FOOT PEDAL DEPRESSED?) */
/**************************************************************************/ status = STATUS & _bios_serialcom(_COM_STATUS, COM1, 0);
    if (status != 0x100) goto TUGGY;
    power = _bios_serialcom (_COM_RECEIVE, COM1, 0);
    if (power == 0x00)
        {
        _clearscreen(_GCLEARSCREEN);
        _settextposition(5,35);
        _settextcolor(9);
        sprintf(buffer, "LASING\n");
        _outtext(buffer);
        laser_loop(pointnow2);
        goto SAVE_DATA;
        }

TUGGY: _asm nop
  }
  goto BOOM;

/**************************************************************************/
SAVE_DATA: _clearscreen(_GCLEARSCREEN);
        _setcolor(14);
        _settextposition(10,12);
        sprintf(buffer,"     DO YOU WISH TO SAVE DATA? (y OR n): ");
        _outtext(buffer);
        c=getch();
        if(c=='Y' || c=='y')
            {
            EMILY: _settextposition(10,12);
            sprintf(buffer,"      ENTER NAME OF OUTPUT FILE: ");
            _outtext(buffer);
            scanf("%s",filename);
            strcat(drive,filename);
            strcat(drive,".dta");

if ((outfile = fopen(drive, "w")) == NULL)
                {
                _settextposition(10,12);
                sprintf(buffer,"*******************FILE ERROR*******************");
                _outtext(buffer);
                getch();
                goto EMILY;
                }
            for (i=1; i<count; i++) fprintf(outfile,"%d     %d\n", temp_point[i], power_point[i]);
            }
}
```

```c
unsigned draw_graph()
 {
  int i, j, c, out_value;
  char buffer[80];

_clearscreen(_GCLEARSCREEN);
  for(i=1,j=0; i<=30; i+=2)
    {
     _settextcolor(10);
     _settextposition(i,1);
     out_value=100-(j*5);
     sprintf(buffer,"%d",out_value);
     _outtext(buffer);
     _settextcolor(12);
     _settextposition(i,75);
     out_value=135-(j*9);
     sprintf(buffer,"%d",out_value);
     _outtext(buffer);
     j=j+1;
     }

_setcolor(9);
  _rectangle(_GBORDER,30,0,590,475);
 } unsigned laser_loop(int test_point)
 {
  unsigned status, send_value, overshoot_control;
  int port_value, c, current_temp, high_set = 0;
  float current_temp2;
  char buffer[80];
  count = 0;
/*************** OVERSHOOT CONTROL ROUTINE ******************/
  if ( test_point > enter_val-10)
         {
           overshoot_control = 3;
           goto CONT;
         }
  if ( test_point <= enter_val-10 && test_point > enter_val-20)
         {
           overshoot_control = 7;
           goto CONT;
         }
  if (test_point <= enter_val -20 && test_point > enter_val-40)
         {
           overshoot_control = 12;
           goto CONT;
         }
  if (test_point <= enter_val-40 && test_point >enter_val -60)
         {
           overshoot_control = 17;
           goto CONT;
         }
  overshoot_control = 25;
/***********************************************************/

CONT: _bios_serialcom(_COM_SEND, COM1, 1);
LOOP: status = STATUS & _bios_serialcom (_COM_STATUS, COM1, 0);
       if (status != 0X100) goto LOOP;
       count = count + 1;
```

```c
        power = 0xff & _bios_serialcom (_COM_RECEIVE, COM1, 0);

if (power == 0xff)
      {
        outp(CS_PORT,1);  /* TURN OFF BUZZER */
        _settextposition(5,20);
        _settextcolor(140);
        sprintf(buffer, "WOULD YOU LIKE TO REVIEW DATA? (y OR n): ");
        _outtext(buffer);
        c=getch();
        if (c=='y' || c=='Y') review_data();
        return;
      } port_value = portv();
    current_temp2 = (port_value/255.)*max_val;
    current_temp2 = (current_temp2-32)*(5./9.);
    current_temp = current_temp2;

/*****************************************/
    temp_point[count] = current_temp;
    power_point[count] = power;
    /*****************************************/ if (current_temp < enter_val-2)
      {
        if ( !high_set && current_temp >= enter_val - overshoot_control)
                send_value = 0;
            else
                send_value = 1;
        _bios_serialcom(_COM_SEND, COM1, send_value);
        light = OFF;
        goto LOOP;
      } if (current_temp > enter_val+2)
      {
        high_set = 1;
        _bios_serialcom(_COM_SEND, COM1, -1);
        light = ON2;
        goto LOOP;
      } high_set = 1;

light = ON;
    _bios_serialcom(_COM_SEND, COM1, 0);
    goto LOOP;
} unsigned review_data()
{
  int c, i, j=1;
  char buffer[80];

TOP: draw_graph();
       j=1;
  BOOM: _setcolor(0);
        _moveto(31,474);
        _lineto(31,1);
```

```
    for(i=32; i<=585; i++)
    {
    _setcolor(0);
    _moveto(i,474);
    _lineto(i,1);

j=j+1;
    if (j >= count)
    {
    getch();
    _clearscreen(_GCLEARSCREEN);
    _settextposition(5,15);
    _settextcolor(4);
    sprintf(buffer,"WOULD YOU LIKE TO REVIEW DATA AGAIN? (y OR n): ");
    _outtext(buffer);
    c=getch();
    if (c=='Y' || c=='y') goto TOP;
    return;
    }

_setcolor(10);
    _moveto(i-1, (459-(459*((temp_point[j-1]-30)/70.)))+1);
    _lineto(i, (459-(459*((temp_point[j]-30)/70.)))+1);

_setcolor(12);
    _moveto(i-1, (459-(459*((power_point[j-1])/135.)))+1);
    _lineto(i, (459-(459*((power_point[j])/135.)))+1);

goto BOOM;
}
```

We claim:

1. A system for welding tissue by irradiation with laser energy, comprising:

laser means for generating a beam of laser energy and directing said beam toward the tissue so as to irradiate a region to be welded and effect welding of said tissue in said region, said laser means having a control input and being responsive to a control signal applied to said control input to adjust the power of aid beam of laser energy, sensor means for sensing the temperature of the tissue in said region to be welded and for providing a sensor output indicative of said temperature, said sensor means comprising an infrared radiation detector for detecting infrared radiation emanating from said region to be welded, said infrared radiation detector detecting infrared radiation which differs in wavelength from the wavelength of said beam of laser energy, and control means, responsive to said sensor output, for supplying a control signal to said laser means such that said region to be welded is heated to a predetermined temperature to effect welding of said tissue in said region.

2. The system for welding tissue by irradiation with laser energy according to claim 1, in which said infrared radiation detector provides an analog signal indicative of the level of infrared radiation sensed, and in which said sensor means further comprises an analog to digital converter, responsive to said analog signal from said infrared radiation detector, for providing said sensor output to said control means as a digital sensor output.

3. The system for welding tissue by irradiation with laser energy according to claim 1, in which said control means comprises a programmed digital computer which supplies a control signal to said laser means to control the power of said beam for welding said tissue in said region.

4. The system for welding tissue by irradiation with laser energy according to claim 1, further comprising indicator means for indicating to the operator whether the sensed temperature in said region to be welded is higher than, lower than, or equal to said predetermined temperature.

5. The system for welding tissue by irradiation with laser energy according to claim 4, in which said indicator means includes means for generating aural indications of whether the sensed temperature in said region to be welded is higher than, lower than, or equal to said predetermined temperature.

6. The system for welding tissue by irradiation with laser energy according to claim 5, in which indicator means provides tones which are characteristic of whether the sensed temperature in said region to be welded is higher than, lower than, or equal to said predetermined temperature.

7. The system for welding tissue by irradiation with laser energy according to claim 1, in which said laser means for generating a beam of laser energy and directing said beam toward the tissue so as to irradiate said region to be welded includes a laser source for generating the laser beam, and a fiber optic conductor for directing the beam toward the tissue to be welded.

8. The system for welding tissue by irradiation with laser energy according to claim 7 in which said fiber optic conductor comprises a single optical fiber for directing said beam toward the tissue so as to irradiate said region to be welded and for returning infrared radiation to said infrared radiation detector from said region to be welded.

9. The system for welding tissue by irradiation with laser energy according to claim 7 in which said fiber optic conductor comprises at least one optical fiber for directing said beam toward the tissue so as to irradiate said region to be welded, and at least one optical fiber for directing said infrared radiation emanating from said region to be welded to said sensor means for sensing the temperature of the tissue in said region to be welded and for providing a sensor output indicative of said temperature.

10. A method for welding tissue by irradiation with laser energy, comprising the steps of:
   generating a beam of laser energy of appropriate power to effect tissue welding,
   directing said beam of laser energy toward the tissue so as to irradiate a region to be welded and effect welding of said tissue in said region,
   sensing the temperature of the tissue in said region to be welded by detecting infrared radiation emanating from said region to be welded and determining said temperature based upon the level of said infrared radiation, said infrared radiation being detected differing in wavelength from the wavelength of said beam of laser energy, and
   adjusting the power of said beam of laser energy such that said region to be welded is heated to a predetermined temperature and said tissue is welded in said region.

11. The method of welding tissue by irradiation with laser energy according to claim 10, further comprising the step of providing an indication of whether the sensed temperature in said region to be welded is higher than, lower than, or equal to said predetermined temperature.

12. The method of welding tissue by irradiation with laser energy according to claim 11 in which the step of providing an indication of whether the sensed temperature in said region to be welded is higher than, lower than, or equal to said predetermined temperature includes the step of providing an aural indication of whether the sensed temperature in said region to be welded is higher than, lower than, or equal to said predetermined temperature.

13. The method of welding tissue by irradiation with laser energy according to claim 12 in which the step of providing an aural indication of whether the sensed temperature in said region to be welded is higher than, lower than, or equal to said predetermined temperature includes the step of providing tones which are characteristic of whether the sensed temperature in said region to be welded is higher than, lower than, or equal to said predetermined temperature.

* * * * *

UNITED STATES PATENT AND TRADEMARK OFFICE
CERTIFICATE OF CORRECTION

PATENT NO.   : 5,409,481
DATED        : April 25, 1995
INVENTOR(S)  : Poppas et al.

It is certified that error appears in the above-indentified patent and that said Letters Patent is hereby corrected as shown below:

On the title page, item:

"[73]   Assignee:    Laserscope" should read

--[73]   Assignee:    Dix Phillip Poppas; Steven Mark Schlossberg; Theodore John Choma; and Scott David Klioze Signed and Sealed this Twenty-third Day of January, 1996

Attest:

BRUCE LEHMAN

Attesting Officer         Commissioner of Patents and Trademarks